United States Patent
Cichocki, Jr.

(10) Patent No.: US 11,311,288 B2
(45) Date of Patent: Apr. 26, 2022

(54) SUTURE NEEDLES HAVING BENDABLE REGIONS

(71) Applicant: Ethicon, Inc., Somerville, NJ (US)

(72) Inventor: Frank Richard Cichocki, Jr., Easton, PA (US)

(73) Assignee: Ethicon, Inc., Somerville, NJ (US)

( * ) Notice: Subject to any disclaimer, the term of this patent is extended or adjusted under 35 U.S.C. 154(b) by 408 days.

(21) Appl. No.: 16/282,604

(22) Filed: Feb. 22, 2019

(65) Prior Publication Data

US 2020/0268378 A1     Aug. 27, 2020

(51) Int. Cl.
| | |
|---|---|
| *A61B 17/06* | (2006.01) |
| *A61B 17/04* | (2006.01) |
| *A61B 17/00* | (2006.01) |

(52) U.S. Cl.
CPC .... *A61B 17/06066* (2013.01); *A61B 17/0469* (2013.01); *A61B 2017/00867* (2013.01); *A61B 2017/06095* (2013.01)

(58) Field of Classification Search
CPC .......... A61B 17/06066; A61B 17/0469; A61B 2017/00867; A61B 2017/006095; A61B 2017/00862
See application file for complete search history.

(56) References Cited

U.S. PATENT DOCUMENTS

| | | |
|---|---|---|
| 3,265,070 A | 8/1966 | Kurtz |
| 4,327,655 A | 5/1982 | Addy et al. |
| 4,981,149 A | 1/1991 | Yoon et al. |
| 5,041,127 A | 8/1991 | Troutman |
| 5,100,432 A * | 3/1992 | Matsutani ........ A61B 17/06066 606/223 |
| 5,219,358 A | 6/1993 | Bendel et al. |

(Continued)

FOREIGN PATENT DOCUMENTS

| | | |
|---|---|---|
| CN | 201755238 | 3/2011 |
| CN | 201782788 | 4/2011 |

(Continued)

OTHER PUBLICATIONS

International Search Report issued in corresponding International Application No. PCT/IB2020/051382, dated Jun. 2, 2020, 4 pages.

*Primary Examiner* — Sarah A Simpson

(57) ABSTRACT

A suture needle having a bendable region includes an elongated body having a proximal section, a distal section, and a bendable region located between the proximal and distal sections. The bendable region has a reduced cross-section and/or is made of a superelastic material that is more flexible than the proximal and distal sections of the elongated body for enabling the suture needle to transform from a first configuration having a larger dimension to a second configuration having a smaller dimension. When in the first configuration, the suture needle is larger than an inner diameter of an elongated conduit of a trocar. In order to pass the suture needle through the elongated conduit of the trocar, the elongated body is bent at the bendable region so that the suture needle is smaller than the inner diameter of the elongated conduit of the trocar. After passing the suture needle through the trocar, the elongated body is bent back to the first, larger dimension to configure the suture needle for use for suturing tissue.

20 Claims, 12 Drawing Sheets

(56) References Cited

U.S. PATENT DOCUMENTS

| | | | |
|---|---|---|---|
| 5,797,961 | A | 8/1998 | Smith et al. |
| 5,897,572 | A | 4/1999 | Schulsinger et al. |
| 5,935,138 | A | 8/1999 | McJames, II et al. |
| 6,322,581 | B1 | 11/2001 | Fakuda et al. |
| 7,727,257 | B2 | 6/2010 | Loubens et al. |
| 8,066,737 | B2 | 11/2011 | Meade et al. |
| 2004/0002724 | A1 | 1/2004 | Falahee |
| 2006/0047309 | A1 | 3/2006 | Cichocki |
| 2012/0010655 | A1* | 1/2012 | Lin ................ A61B 17/062 606/223 |

FOREIGN PATENT DOCUMENTS

| | | |
|---|---|---|
| CN | 204839615 | 12/2015 |
| CN | 204863323 | 12/2015 |
| CN | 206777363 | 12/2017 |
| WO | 2006065913 | 6/2006 |

* cited by examiner

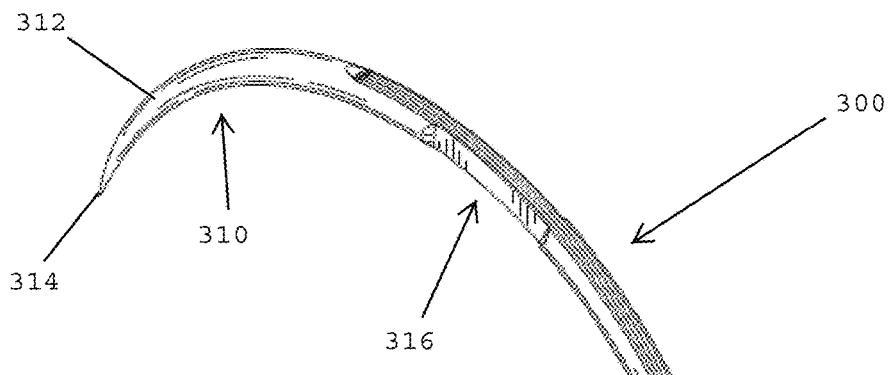
FIG. 13A
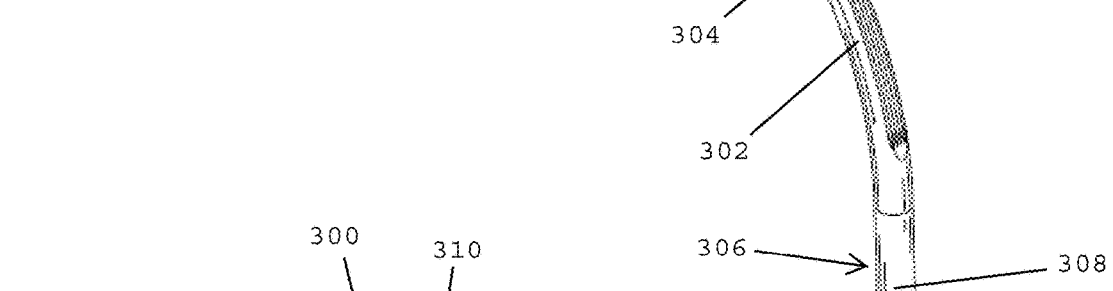
FIG. 13B
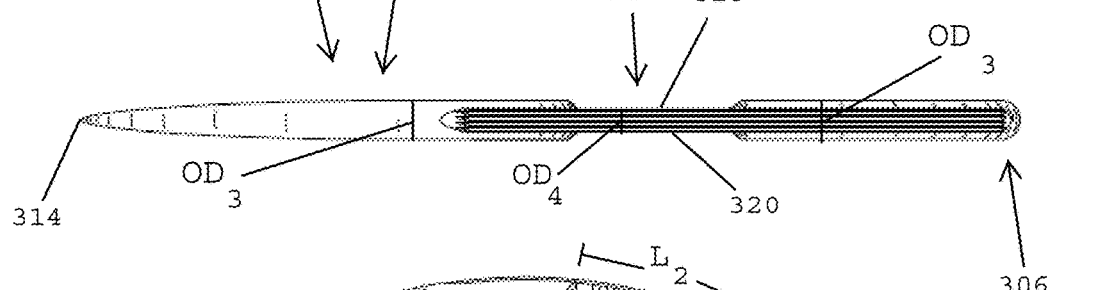
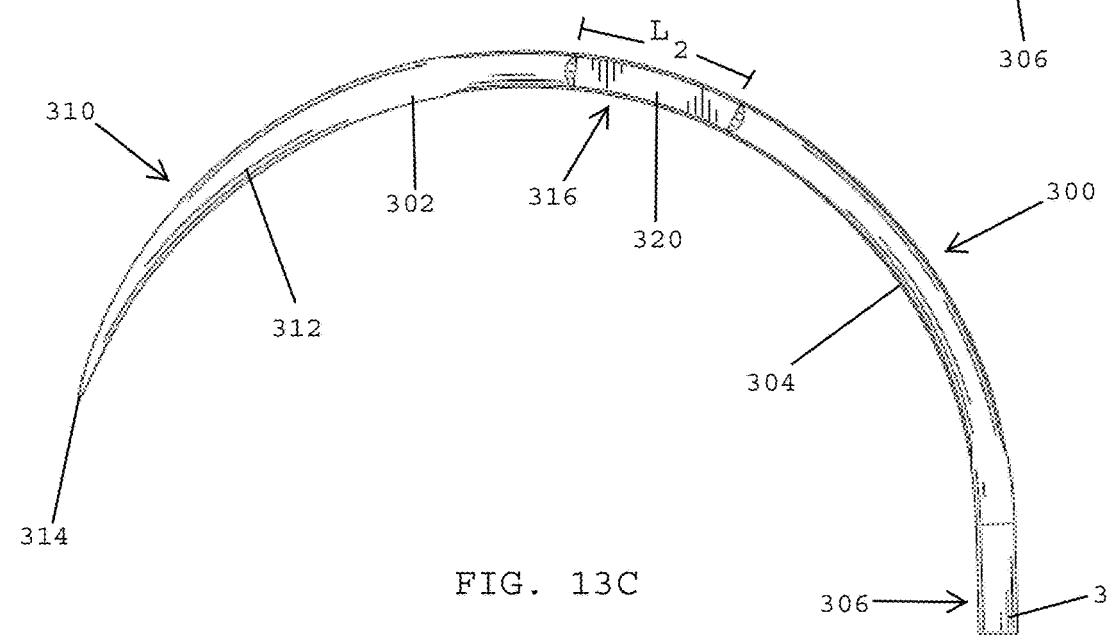
FIG. 13C

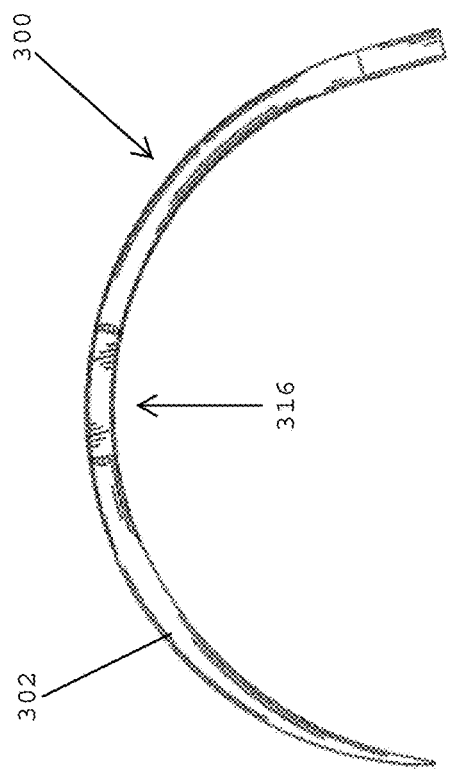
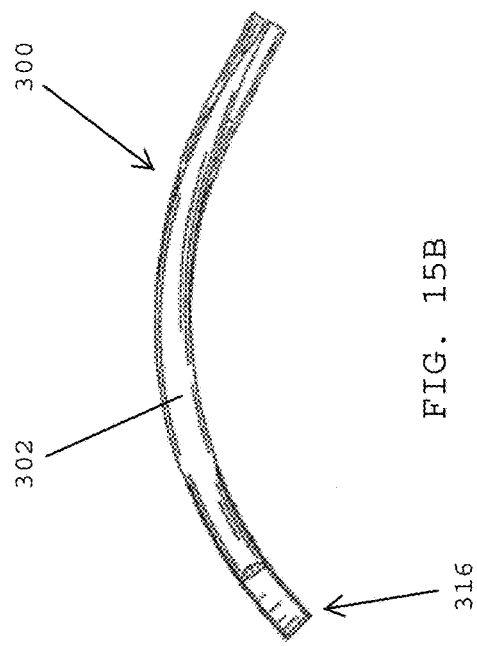
FIG. 15A
FIG. 15B
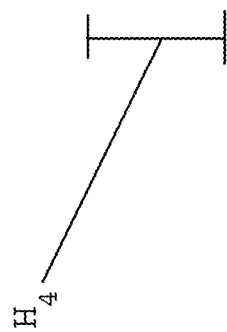

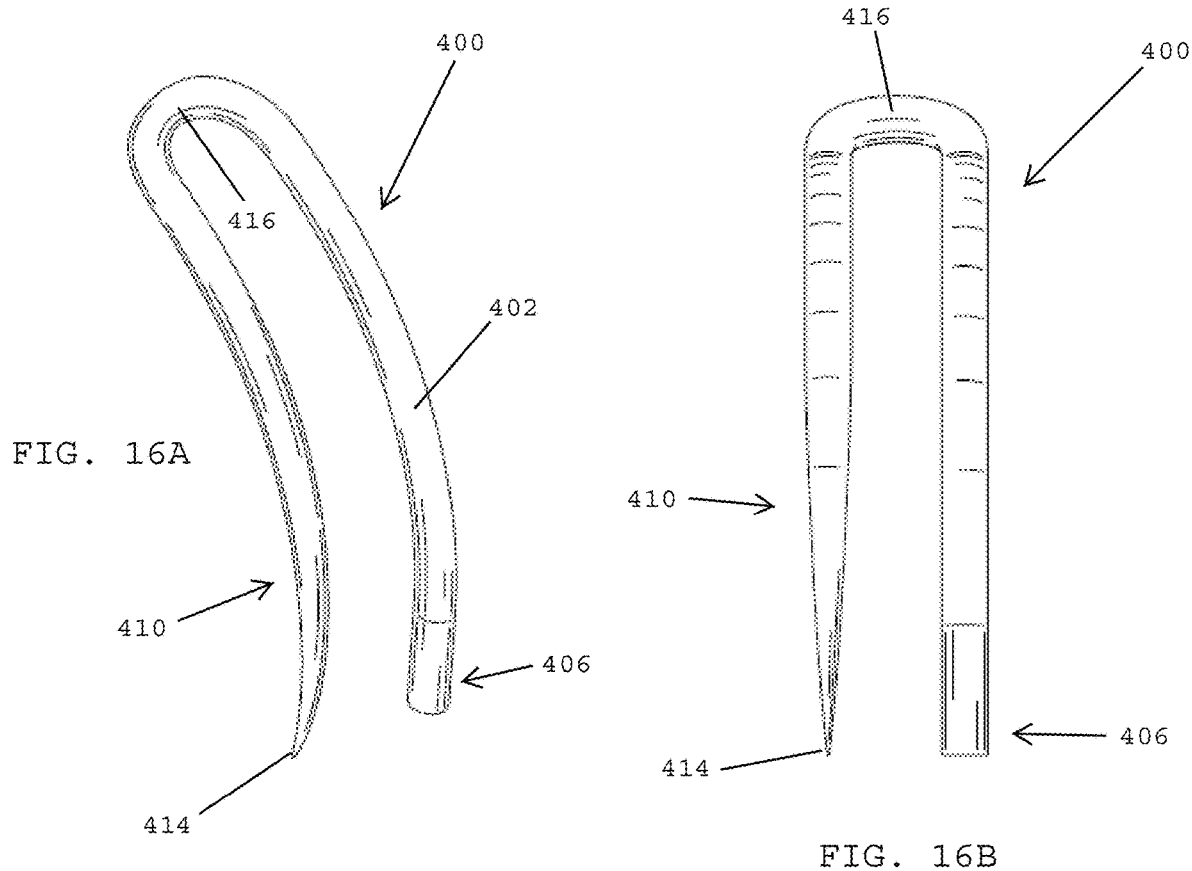
FIG. 16A
FIG. 16B
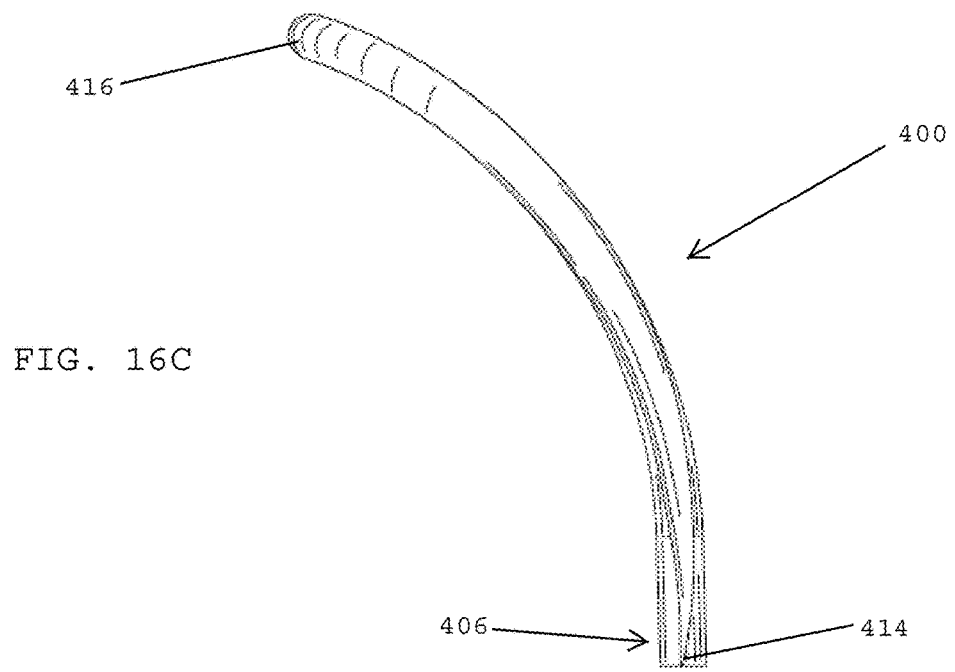
FIG. 16C

SUTURE NEEDLES HAVING BENDABLE REGIONS

BACKGROUND OF THE INVENTION

Field of the Invention

The present patent application is generally related to surgical procedures and surgical tools, and is more specifically related to needles used for suturing tissue.

Description of the Related Art

Surgeons use trocars and cannulas to position surgical tools, such as suture needles, at surgical sites. The size of a suture needle that can be passed through the cannula to a surgical site is limited by the size of the opening in the cannula. In many instances, surgeons desire to use larger curved needles for closing surgical wounds and repairing anatomical features, however, passing the larger needles through smaller trocars is difficult. For example, 5 mm trocars are often used during minimally invasive surgeries (MIS), however, surgeons cannot pass the larger curved suture needles through the 5 mm trocars so they are forced to use only smaller suture needles.

The smaller suture needles are less than optimal because, inter alia, they often require a surgeon to make many more passes of the needle and suture through tissue, which lengthens the surgical procedure and can frustrate the surgeon. Using smaller needles may also produce a bite distance that puts the wound or anatomical feature at risk of dehiscence.

In addition, larger-sized sutures cannot be easily attached to the smaller suture needles. Thus, when fine sutures are passed through tissue with a smaller bite size, a cheese wire effect may result, whereby the suture cuts through the tissue it is intended to hold.

Thus, there is a need for improved suture needles that may be passed through relatively smaller trocars (e.g., 5 mm trocars) that are used in surgical procedures. There is also a need for systems, devices and methods for passing larger suture needles through the relatively smaller trocars.

SUMMARY OF THE INVENTION

In one embodiment, a suture needle preferably has a bendable and/or flexible region that is designed to enable easy bending and reshaping of the needle to fit through a trocar, such as a small trocar (e.g., a 5 mm trocar). The suture needle having the bendable and/or flexible region desirably enables the needle to be shaped to fit through the trocar, and, after being passed through the trocar to a surgical site, reshaped to desired curvature (e.g., a semi-circular configuration, a half-circle configuration) that facilitates suturing tissue.

In one embodiment, a suture needle has a bendable region that is more flexible and/or malleable than proximal and distal sections of the needle that bound the bendable region. In one embodiment, the bendable region may be formed by providing a section on the needle that has a reduced cross-sectional dimension, such as in the X-direction (e.g., the side surfaces of the needle) or the T-dimension (e.g., the top and bottom surfaces of the needle).

In one embodiment, a suture needle including a bendable region having a reduced cross-sectional dimension in the X-direction may be folded sideways on itself by about 180 degrees so that the needle point at the distal end of the needle is located near to the needle barrel at the proximal end of the needle. In one embodiment, in a normal, unfolded configuration, the suture needle has an outer dimension that is too large for being safely and efficaciously passed through a trocar. Thus, the suture needle may be folded into a needle having a smaller outer dimension for being passed through the trocar. After the folded needle has been passed through the trocar to a surgical site, the needle may be re-shaped back to the original normal, unfolded configuration (e.g., a half-circle, a semi-circular shape) for use during surgery while still exhibiting substantial strength in surgical bending. For example, for a suture needle having a reduced cross-sectional dimension in the X-direction, the suture needle maintains substantial strength in surgical bending since the T-dimension has not been reduced and may even have been increased via the barreling that occurs with needle flat formation along the x-direction.

In one embodiment, a suture needle having a bendable region preferably includes an elongated body having a proximal section with a suture attachment hole and a distal section with a sharpened tip. In one embodiment, the elongated body desirably has a bendable region located between the proximal and distal sections. In one embodiment, the bendable region of the elongated body is preferably more flexible than the proximal and distal sections of the elongated body for enabling the elongated body of the suture needle to be transformed from a first configuration having a greater dimension and a second configuration having a smaller dimension.

In one embodiment, the elongated body has a greater height when in the first configuration and a smaller height when in the second configuration.

In one embodiment, the elongated body has a semi-circular shape when in the first configuration and a seagull shape or a folded shape when in the second configuration.

In one embodiment, when the elongated body has been bent into the seagull shape configuration, the proximal section of the elongated body preferably defines a proximal arc, the distal section of the elongated body preferably defines a distal arc, and the bendable region of the elongated body preferably defines a V-shaped section that interconnects inner ends of the proximal and distal arcs. In the seagull shaped configuration, the proximal arc, the distal arc, and the V-shaped section preferably lie in a common plane.

In one embodiment, when the elongated body has been bent into the folded configuration, the elongated body is folded in half so that the proximal section of the elongated body preferably lies in a first plane and the distal section of the elongated body preferably lies in a second plane that is different than the first plane. In the folded configuration, the bendable region desirably interconnects inner ends of the proximal and distal sections of the elongated body. In one embodiment, with the elongated body in the folded shape, the sharpened tip of the distal section of the elongated body is preferably adjacent the suture attachment hole of the proximal section of the elongated body.

In one embodiment, the proximal and distal sections of the elongated body desirably define a first outer diameter and the bendable region of the elongated body preferably defines a second outer diameter that is smaller than the first outer diameter of the respective proximal and distal sections.

In one embodiment, the bendable region preferably includes one or more flat surfaces located on opposite sides of the elongated body that define a reduced cross-sectional region of the elongated body having a dimension that is smaller than the first outer diameter of the respective proximal and distal sections of the elongated body.

In one embodiment, the one or more flat surfaces may include first and second flat surfaces located on respective first and second lateral sides of the elongated body. In one embodiment, the one or more flat surfaces may include first and second flat surfaces located on respective top and bottom sides of the elongated body.

In one embodiment, the bendable region of the elongated body is preferably made of a superelastic material having shape memory properties, and the proximal and distal sections of the elongated body may be made of a second material that is more rigid and less elastic than the superelastic material having shape memory properties. In one embodiment, the superelastic material may include Nitinol and the more rigid, second material may include medical grade or biocompatible stainless steel.

In one embodiment, a suture needle having a bendable region preferably includes an elongated body having a proximal section with a suture attachment hole and a distal section with a sharpened tip. In one embodiment, the elongated body desirably has a bendable region located between the proximal and distal sections. In one embodiment, the bendable region of the elongated body desirably includes a superelastic material and the proximal and distal sections of the elongated body desirably include a second material that is more rigid and less elastic than the superelastic material for enabling the suture needle to be transformed from a first configuration having a greater dimension (e.g., a greater height) and a second configuration having a smaller dimension (e.g., a smaller height).

In one embodiment, the elongated body has a semi-circular shape and a greater height when in the first configuration and a seagull shape with a smaller height when in the second configuration.

In one embodiment, the elongated body has a semi-circular shape and a greater height when in the first configuration and a folded shape with a smaller height when in the second configuration.

In one embodiment, a method of passing a suture needle through a trocar desirably includes obtaining a suture needle with an elongated body having a proximal section, a distal section, and a bendable region located between the proximal and distal sections, whereby the bendable region of the elongated body is more flexible than the proximal and distal sections of the elongated body.

In one embodiment, a method of passing a suture needle through a trocar desirably includes positioning the suture needle adjacent an end of a trocar having an elongated conduit with an inner diameter, and bending the elongated body at the bendable region thereof to transform the elongated body from a first dimension that is greater than the inner diameter of the elongated conduit of the trocar to a second dimension that is less than the inner diameter of the elongated conduit of the trocar In one embodiment, a method of passing a suture needle through a trocar preferably includes after bending the elongated body to the second dimension that is less than the inner diameter of the elongated conduit of the trocar, passing the suture needle through the elongated conduit of the trocar.

In one embodiment, a method may include, after passing the suture needle at the second dimension through the trocar, again bending the elongated body at the bendable region thereof to transform the elongated body from the second dimension that is less than the inner diameter of the elongated conduit of the trocar to the first dimension that is greater than the inner diameter of the elongated conduit of the trocar.

In one embodiment, instead of providing a needle with a local body flat, a small cut may be made in a section of the needle to reduce the effective cross-sectional dimension of the needle at the location of the cut.

In one embodiment, the needle may be provided in the bent and/or folded configuration in a package so that the needle is immediately ready to pass through the trocar once it is removed from the package. In one embodiment, after passing the needle through a trocar to a surgical site, the needle may be re-shaped to a larger configuration (e.g., a semi-circular configuration) whereupon the needle will exhibit substantial strength in surgical bending since the T-dimension has not been reduced, and may even have been increased via the barreling that occurs with needle flat formation along the x-direction.

In one embodiment, a suture needle having a bendable region may be provided using a heat treatment. The heat treatment may soften the alloy used to make the needle and may provide increased reshape ductility. In one embodiment, a temperature in the range of 700 to 1100 Celsius may be used to achieve the softening of the bendable region of the needle. In one embodiment, the bendable region of the needle is subject to heat treatment for making the bendable region more flexible and/or malleable, while proximal and distal sections of the needle are not subject to heat treatment so that the proximal and distal sections are more rigid than the bendable region. In one embodiment, the heat treatment disclosed herein may be used on a needle having a reduced diameter region to provide a needle having a bendable region.

In one embodiment, a suture needle having a bendable region may include a composite needle made of multiple materials. In one embodiment, the bendable, composite suture needle may include a softer, more flexible material (e.g., Nitinol) for the bendable region, while the remaining portions of the needle (e.g., the proximal and distal sections) are made of more rigid, less flexible material (e.g., stainless steel).

In one embodiment, the reshape ductility of the bendable region of the suture needle preferably exceeds the reshape ductility of the proximal or distal sections of the suture needle so that the proximal and distal sections of the needle are sufficiently rugged for withstanding the multiple reshapes required for trocar passage.

In one embodiment, the yield force of the bendable region of the suture needle may exhibit onset yield point properties similar to those found in superelastic materials having shape memory properties such as Nitinol superelastic needles, which have been widely accepted by surgeons for use in laparoscopic surgery.

In one embodiment, a bendable suture needle having a bendable region may be marked (e.g., via laser marking) for easy identification, such as with a laser marking or a thermal marking.

In one embodiment, heat treatment methodologies used to produce a suture needle having a bendable region may include using electrical resistance, flame, induction heating, conduction via hot contacts and the like.

In one embodiment, a suture needle is more economical to make because only the bendable portion of the needle is made of a superelastic material (e.g., Nitinol), while the remainder of the needle (e.g., the proximal and distal sections) may be made of less expensive or rugged materials (e.g., stainless steel).

In one embodiment, the bendable suture needle disclosed herein may be safer to use because safety issues associated with storing spring energy is superelastic and Nitinol needles during trocar passage may be avoided.

In one embodiment, a larger sized needle may be provided (e.g., a CTX needle) that can still pass through a smaller trocar (e.g., a 5 mm trocar). Due to the presence of a bendable region on the needle, after the larger needle has passed through the trocar, it may be reshaped to a larger configuration (e.g., a semi-circular configuration) via bending at the localized region using laparoscopic instruments.

In the larger configuration (e.g., a semi-circular configuration), a surgeon may use the suture needle to perform a suturing operation. At the end of the suturing operation, the needle preferably continues to exhibit substantial ductility at the bendable region so that it can be bent or folded into a smaller shape for extraction through the smaller diameter trocar (e.g., 5 mm trocar).

In one embodiment, the location of the bendable/flexible region of the needle along the length of the needle may be offset from a mid-point of the needle depending upon the size of the needle and the desired trocar size through which the needle will be passed.

In one embodiment, relative to the flexible/bendable region, the majority of the length of the needle may be made of a relatively harder, stronger, more rigid, and/or less flexible material (e.g., stainless steel) to resist damage to the needle, with only the flexible/bendable region having increased bendability. Providing a suture needle having the above properties yields a laparoscopic needle with desirable attributes that behaves largely like conventional, high strength needles. In one embodiment, providing a proximal end of a needle made of stainless steel and similar materials makes it more economical and efficient to attach sutures to the proximal end, because it has been found to be more difficult and expensive to attached sutures to suture attachment holes formed in superelastic and Nitinol needles.

In one embodiment, the bendable region of the suture needle may be made to mimic the onset yield point of a superelastic material or shape memory alloy (e.g., Nitinol), thus providing a surgically acceptable level of flexibility without the cost and processing challenges associated with making the entire needle out of the superelastic material (e.g., Nitinol). Surgeons largely agree that superelastic nitinol needles exhibit adequate strength for most laparoscopic surgery even though needle bending strength data indicates that the yield point can be substantially lower than that exhibited by stainless steel needle alloys. Thus, only a small length or section of the suture needle disclosed in the present patent application would need to exhibit a low yielding force.

Reshaping a needle exhibiting a localized area for improved bending with laparoscopic instruments is much easier than reshaping a conventional suture needle having uniform high strength properties. Reshaping the needle in the surgical cavity is possible at low forces in a way that does not frustrate the surgeon and minimizes the potential for patient harm that can occur through needle sticks during reshaping high strength suture needles.

The cost of materials and processing difficulty of steel needles with a localized region for bending is much lower than the cost of materials and processing required with nitinol needles. In one embodiment, the cost of goods is lower than needles produced from 100% superelastic materials (e.g., Nitinol).

In one embodiment, only the bendable region of the suture needle is made of the superelastic material so that a more robust suture attachment may be achieved at the proximal end of the needle, made of stainless steel, than is possible with superelastic materials (e.g., Nitinol).

In one embodiment, patient harm due to inadvertent needle detachment while a superelastic suture needle is under spring tension at the mouth of the trocar may be avoided. Moreover, damage to the seal of the trocar caused by the spring tension of a superelastic needle may be avoided.

In one embodiment, initial reshaping of the needle at the factory, in concert with a softening heat treatment or material removal in a localized region, may be conducted so that the needle may be dispensed from the suture package already in a "seagull" shaped curvature or a folded in half configuration. Providing a pre-shaped suture needle preferably reduces the number of steps a surgeon must perform to pass the needle through a trocar and ensures that the right curvature is established out of the package to enable effective passage of larger needles through relatively smaller trocars (e.g., a 5 mm trocar).

In one embodiment, larger needles (e.g., CTX sized needles) having a bendable region may be passed through a small 5 mm trocar. Enabling the use of larger needles through smaller trocars preferably results in many benefits including the option to use any trocar positioned at any location during surgery since the needles will work with 5 mm, 8 mm, 10 mm, and 12 mm standard trocars. Moreover, smaller incisions associated with 5 mm trocar ports make the trocar port wound much easier to close and provides the patient with many benefits including 1) lower risk of incisional hernia, 2) better cosmesis, 3) less pain, and 4) lower risk of infection.

In one embodiment, premium alloys such as ETHALLOY, 4310 and the like may be used and combined with robust taper point designs (e.g. 6:1, or 8:1 tapers) to provide damage resistance in a manner that is competitive with nitinol shape memory needle points. Stout taper ratios also desirably minimize the likelihood of needle points scraping the inside wall of the trocar. The suture needles having bendable regions also desirably provide excellent damage resistance in robotic surgery and MIS surgery where extreme stresses can be applied to needles.

In one embodiment, during manufacturing and prior to being inserted into a package for shipment and storage, the suture needle may be pre-shaped into a "seagull" configuration so that it is first presented to a surgeon in the straightened, seagull configuration. The "seagull" shaped needle may be passed through a trocar without substantial flex or friction because the needle has outer dimensions that are smaller than the inner diameter of a 5 mm trocar. After the seagull shaped needle has been passed through the trocar for being delivered to the surgical site, gripping tools (e.g., needle drivers) may be used to re-shape the needle to a curved configuration (e.g., a semi-circular or half-circle shape) so that the needle may be used for surgery. After surgery, in order to remove the needle from the body, a surgeon may re-shape the needle into a "seagull" configuration (e.g., with needle drivers) so it may be easily removed from the surgical cavity via the trocar.

In one embodiment, the "bendable region" of the suture needle may be formed via heat treatment of martensitic, martensitic-aged, or austenitic steel alloys or the like.

In one embodiment, the bendable region may also be formed by reducing the cross-section of the needle at the bendable region. In one embodiment, the bendable region may be provided by forming one or more local body flats that effectively reduce the needle T-dimension or X-dimension.

In one embodiment, in order to maximize ductility at the bendable region of the needle, the length of the bendable region of the suture needle is preferably equal to or greater that the wire diameter of the needle.

In one embodiment, the softened or bendable region may be in the middle of the needle or offset from the middle of the needle (e.g., somewhat closer to the point or barrel). In one embodiment, the bendable region of the needle may be located midway along the length of the needle between the distal tip and the proximal end of the needle.

In one embodiment, the bendable region of the needle is located closer to the distal end than the proximal end of the needle. In one embodiment, the space before the start of the tapered region of the needle provides a location for grasping the needle to reshape the needle. In one embodiment, locating the bendable region closer to the distal tip than the proximal end may result in the needle in the seagull configuration suffering less point damage as it passes through the trocar. In one embodiment, locating the bendable region closer to the distal tip than the proximal end may result in the needle being stronger in surgical use since the bendable feature is nearer to the distal point and a somewhat lower bending moment at the weak location may occur.

In one embodiment, a suture needle may have a bendable region that is located closer to the proximal end of the needle than the distal end of the needle, which preferably provides a needle that is less likely to suffer suture damage as it passes through the trocar in the seagull configuration.

These and other preferred embodiments of the present patent application will be described in more detail below.

BRIEF DESCRIPTION OF THE DRAWINGS

FIG. 13A shows a perspective view of a suture needle having a bendable region located between a proximal end and a distal end of the needle, in accordance with one embodiment of the present patent application.

FIG. 13B shows a top plan view of the suture needle shown in FIG. 13A.

FIG. 13C shows a side view of the suture needle shown in FIGS. 13A and 13B.

FIG. 15A shows a first stage of a method for passing the suture needle of FIGS. 13A-13C and 14A-140 through a trocar, in accordance with one embodiment of the present patent application.

FIG. 15B shows a second stage of a method of passing the suture needle of FIG. 15A through a trocar, in accordance with one embodiment of the present patent application.

FIG. 16A shows a perspective view of a suture needle having a bendable region whereby the suture needle is in a bent configuration, in accordance with one embodiment of the present patent application.

FIG. 16B shows an end view of the bent suture needle shown in FIG. 16A.

FIG. 16C shows a side view of the bent suture needle shown in FIGS. 16A and 16B.

DETAILED DESCRIPTION OF PREFERRED EMBODIMENTS

Figure 1A:
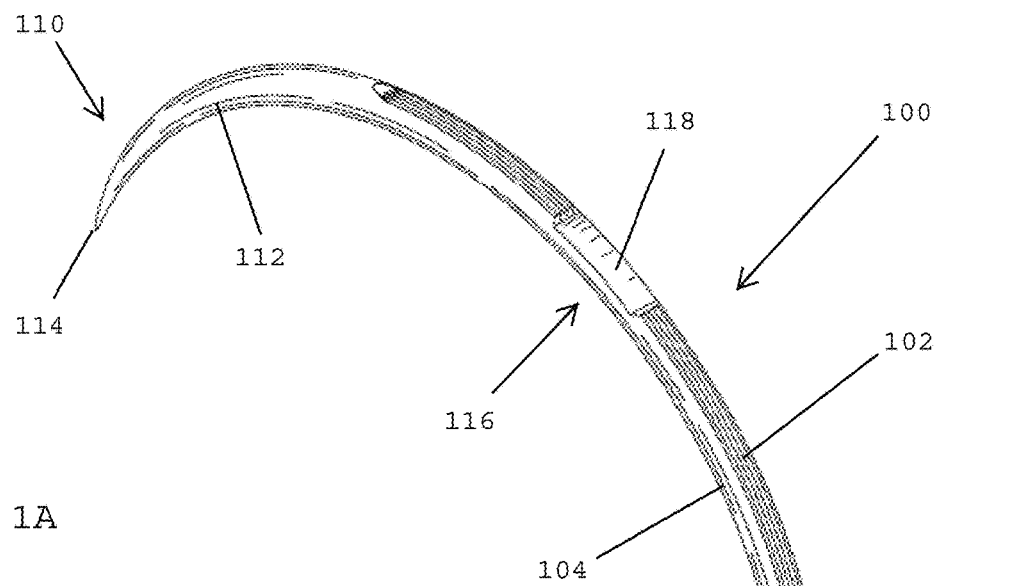
FIG. 1A shows a perspective view of a suture needle having a bendable region, in accordance with one embodiment of the present patent application.
Figure 1B:
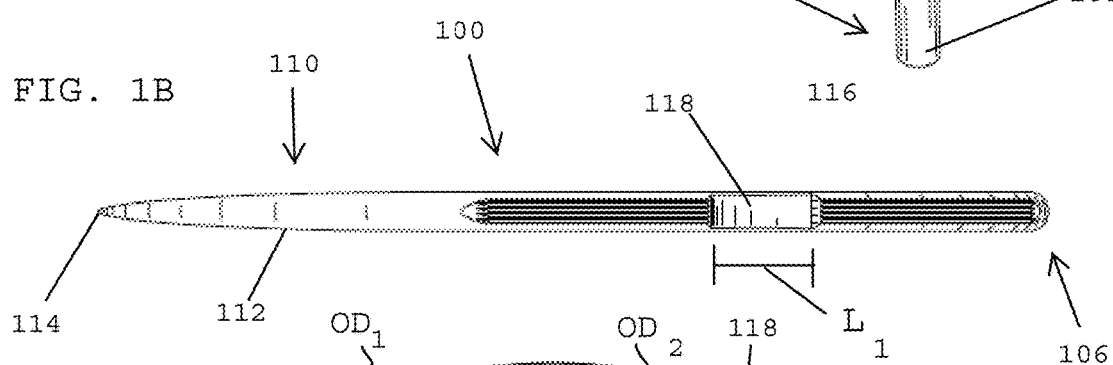
FIG. 1B shows a top plan view of the suture needle shown in FIG. 1A.
Figure 1C:
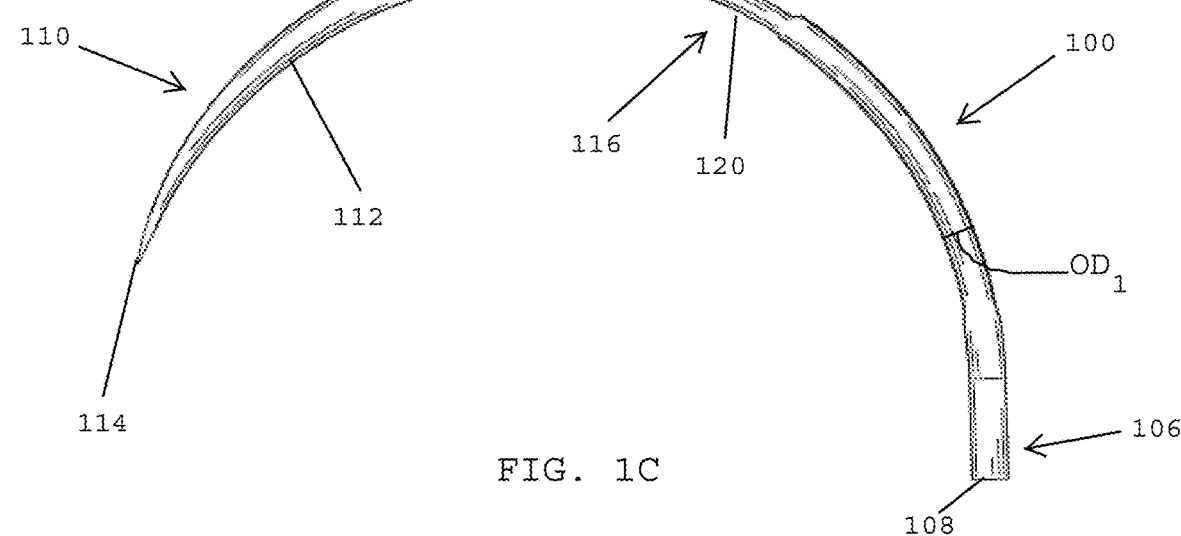
FIG. 1C shows a side view of the suture needle shown in FIGS. 1A and 1B.

Referring to FIGS. 1A-1C, in one embodiment, a suture needle 100 preferably includes an elongated body 102 having an outer surface 104. The elongated body 102 preferably has a proximal end 106 with a suture mounting barrel 108 having a hole for receiving a suture (not shown) and a distal end 110 with a tapered region 112 having a sharpened point or tip 114.

In one embodiment, the suture needle 100 preferably includes a bendable section or region 116 that is located between the proximal end 106 and the distal end 110 of the elongated body 102. In one embodiment, the bendable region 116 is preferably positioned along the length of the needle, between the proximal and distal ends thereof. In one embodiment, the bendable region is more bendable and/or flexible than other regions of the needle, and particularly the proximal and distal sections of the needle.

In one embodiment, the bendable region may be formed by reducing a cross-section of the needle, by making the bendable region of a material that is more flexible than the material used to make the proximal and distal sections of the needle, and/or my treating the bendable region with heat to soften the material of the bendable region to make it more flexible than the proximal and distal sections.

In one embodiment, the bendable region 116 may include a reduced cross-sectional area of the elongated body 102 of the suture needle 100. In one embodiment, the reduced cross-sectional area is formed with a first flat surface 118 located on a top side of the elongated body 102 and a second flat surface 120 located on an underside of the elongated body 102.

In one embodiment, the bendable region 116 preferably has a smaller diameter than the proximal end 106 and the distal end 110 of the elongated body 102, which are located on opposite sides of the bendable region 116. In one embodiment, the proximal and distal sections 106, 110 of the elongated body 102 preferably have respective outer diameters $OD_1$ that are greater than the outer diameter $OD_2$ of the bendable region 116, which is defined by the first and second flat surfaces 118, 120.

In one embodiment, the bendable region 116 has a length $L_1$ that is preferably equal to or greater than the outer diameter $OD_1$ of the proximal and distal sections 106, 110 of the elongated body 102 of the suture needle 100.

Figure 2A:
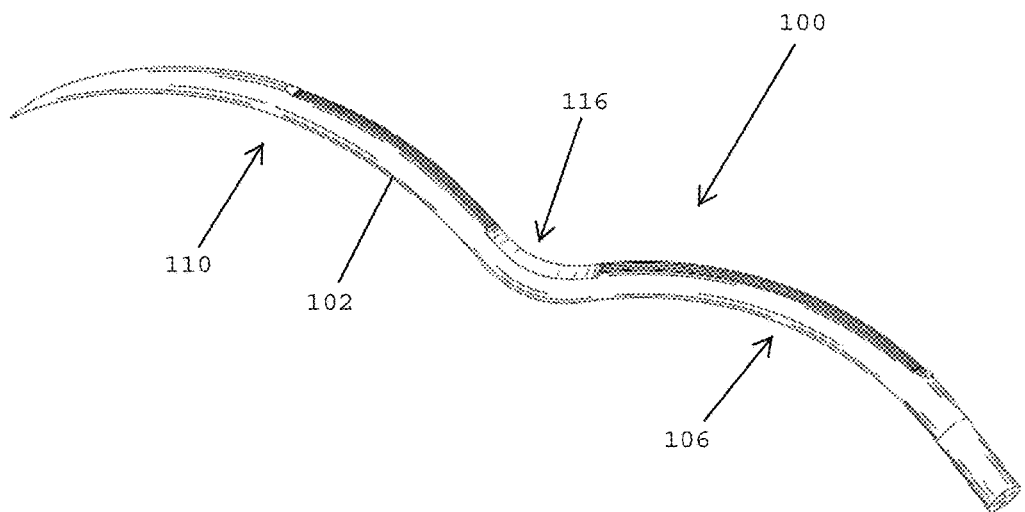
FIG. 2A shows a perspective of the suture needle shown in FIGS. 1A-1C after the needle has been bent in the bendable region, in accordance with one embodiment of the present patent application.
Figure 2B:
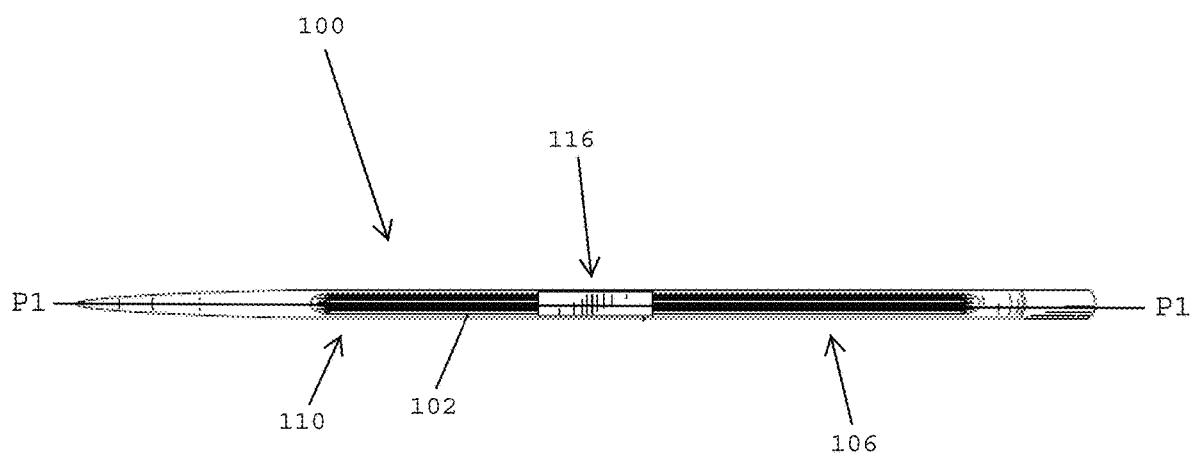
FIG. 2B shows a top plan view of the suture needle shown in FIG. 2A.
Figure 2C:
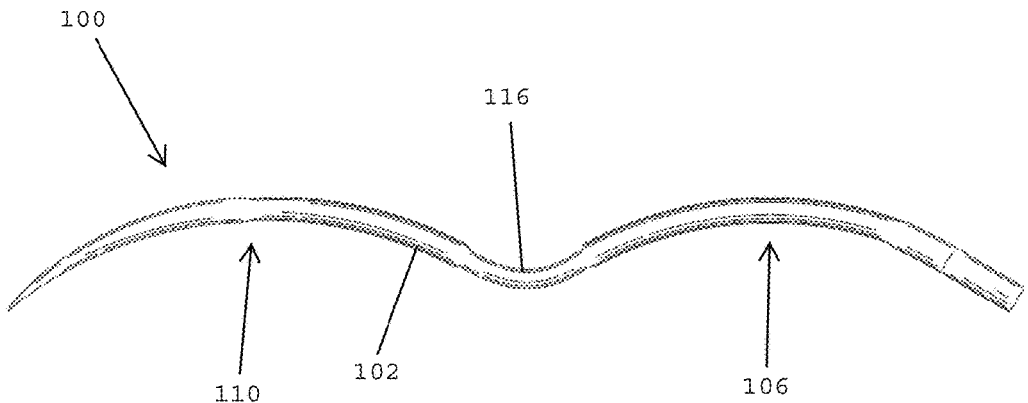
FIG. 2C shows a side view of the suture needle shown in FIGS. 2A and 2B.

Referring to FIGS. 2A-2C, in one embodiment, the bendable region 116 of the suture needle 100 may be bent to provide a bent suture needle having a seagull shaped configuration. In one embodiment, the needle may be repeatedly transformed back and forth between the semi-circular or half-circle shaped configuration shown in FIG. 10 and the seagull shaped configuration shown in FIG. 2C. In one embodiment, as the suture needle 100 is bent into the seagull shaped configuration, the proximal section 106 and the distal section 110 of the needle, which are desirably more rigid than the bendable region 116, remain unchanged in their respective configurations.

In one embodiment, when the elongated body 102 has been bent into the seagull shape configuration of FIGS. 2A-2C, the proximal section 106 of the elongated body 102 preferably defines a proximal arc, the distal section 110 of the elongated body 102 preferably defines a distal arc, and the bendable region 116 of the elongated body 102 preferably defines a U-shaped section that interconnects inner ends of the proximal and distal arcs. In the seagull shaped configuration, the proximal arc, the distal arc, and the V-shaped section preferably lie in a common plane P1 (FIG. 2B).

Providing a suture needle with a bendable region (i.e., a region that is more flexible or bendable than adjacent sections of the needle) preferably enables surgical personnel to reduce the overall height and/or dimension of the suture needle so that it may be passed through smaller trocars that are typically used in minimally invasive surgeries (MIS), such as 5 mm trocars.

Figure 3:
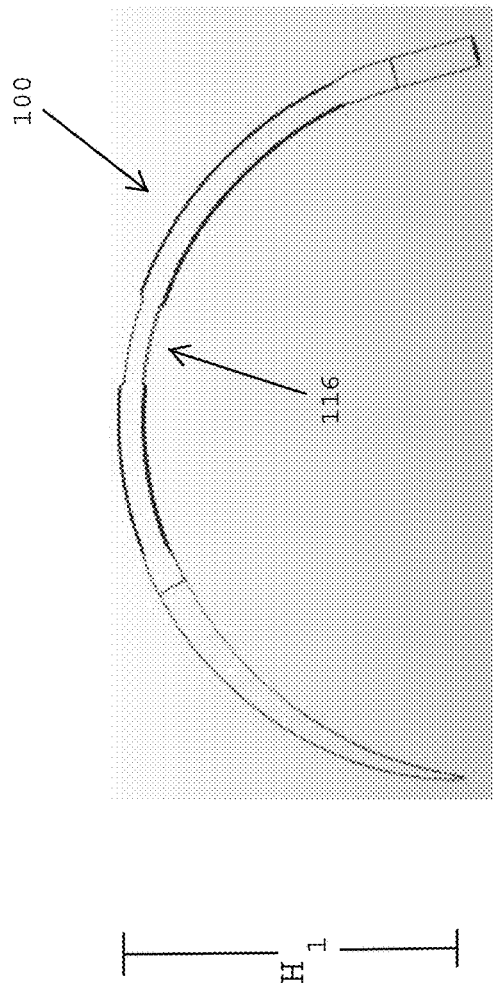
FIG. 3 shows a side view of a suture needle in an unbent configuration, in accordance with one embodiment of the present patent application.
Figure 4:
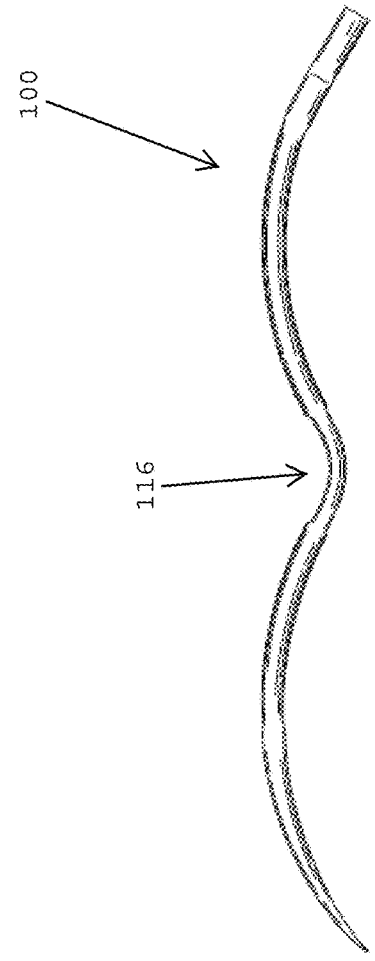
FIG. 4 shows the suture needle of FIG. 3 in a bent configuration, in accordance with one embodiment of the present patent application.

A comparison of the height change that may be made to the suture needle 100 may be seen in FIGS. 3 and 4. Referring to FIG. 3, in one embodiment, prior to being bent, the suture needle 100 has a height $H_1$ of greater than 5 mm, more preferably about 10-15 mm, and even more preferably about 13 mm. Referring to FIG. 4, in one embodiment, after the suture needle 100 has been bent at the bendable region 116 into the lower profile, seagull shaped configuration, the suture needle has a height $H_2$ of about 5 mm or less, which is less than the height $H_1$ of the higher profile suture needle 100 shown in FIG. 3. Thus, when the suture needle 100 has the higher profile shown in FIG. 3, the suture needle may not pass through a smaller trocar (e.g., 5 mm trocar), however, when the suture needle 100 has the lower profile shown in FIG. 4, the suture needle may be readily passed through the smaller trocar.

Figure 5:
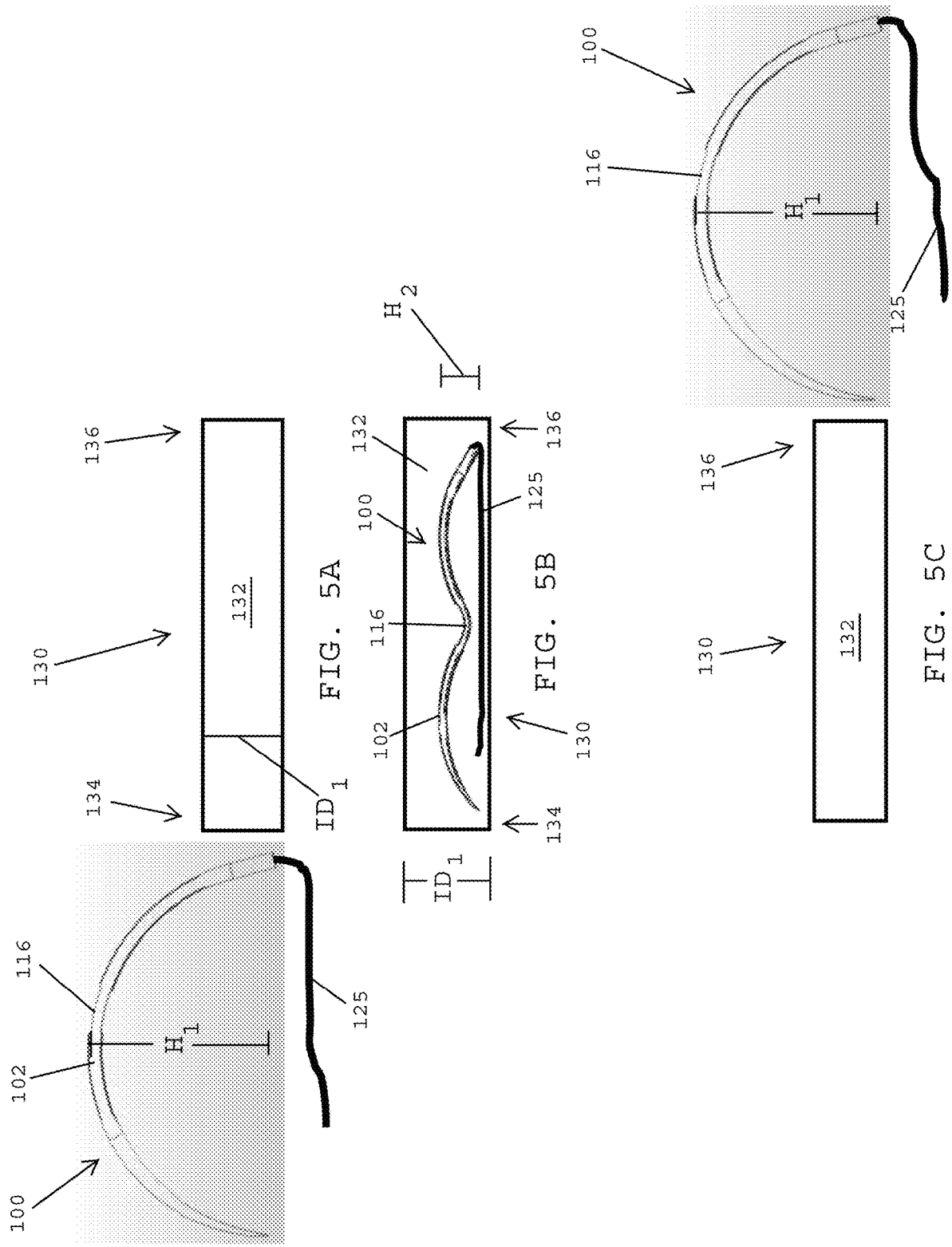
FIG. 5A shows a first step of a method of passing a suture needle through a trocar, in accordance with one embodiment of the present patent application.
FIG. 5B shows a second state of a method of passing a suture needle through a trocar, in accordance with one embodiment of the present patent application.
FIG. 5C shows a third stage of a method of passing a suture needle through a trocar, in accordance with one embodiment of the present patent application.

In one embodiment, the suture needle having the bendable region may be transformed from an unbent, semi-circular configuration to a bent, seagull shaped configuration for passing through a trocar, such as a 5 mm trocar used in minimally invasive surgery. Referring to FIG. 5A, in one embodiment, the suture needle 100 with the bendable region 116 is in an unbent configuration so that the elongated body 102 of the suture needle defines a relatively higher profile height $H_1$ of about greater than 5 mm, more preferably about 10-15 mm, and even more preferably about 13 mm. The suture needle 100 has a suture 125 secured to a proximal end thereof. The suture needle 100 may be juxtaposed with a trocar 130 with the proximal end of the suture needle (i.e., the end attached to the suture) defining the leading end of the needle that is passed through the trocar. The trocar 130 (e.g., a 5 mm trocar) may have an elongated conduit 132 that extends from a first opening at a first end 134 of the trocar to a second opening at a second end 136 of the trocar. The elongated conduit 132 of the trocar 130 preferably has an inner diameter $ID_1$ that is smaller than the height $H_1$ of the elongated body 102 of the unbent suture needle 100. As a result, the unbent suture needle 100 has a profile and/or height that is too large to pass through the elongated conduit 132 of the trocar 130.

Referring to FIG. 5B, in one embodiment, the suture needle 100 shown in FIG. 5A may be bent at the bendable region 116 into a seagull shaped configuration so that the elongated body 102 of the suture needle 100 now has a height $H_2$ (e.g., 5 mm) that is less than the height $H_1$ and the inner diameter $ID_1$ of the elongated conduit 132 of the trocar 130. As a result, in the bent configuration of FIG. 5B, the suture needle 100 may be easily passed into the first opening at the first end 134, advanced through the elongated conduit 132, and removed from the second opening at the second end 136 of the trocar, for being positioned at a surgical site inside a patient. As noted above, the proximal end of the suture needle 100 that is attached to the suture 125 is preferably the leading end of the needle as the needle is passed through the trocar and the tip of the suture needle trails the proximal end, which preferably minimizes the likelihood of needle sticks to organs or tissue upon introduction of the needle into the surgical cavity. In one embodiment, the suture needle is grasped by a needle driver for passing the suture needle through the trocar 130.

Referring to FIG. 5C, in one embodiment, after the bent suture needle shown in FIG. 5B has been removed from the second opening at the second end 136 of the trocar 130, a surgeon may utilize surgical tools (e.g., a needle driver) to transform and/or reshape the suture needle 100 from the bent configuration (FIG. 5B) back to the original, unbent, semi-circular configuration having the height $H_1$. The suture needle 100 in the original semi-circular shape may be utilized for suturing tissue. At that end of a suturing operation, a surgeon may once again bend the bendable region 116 of the suture needle 100 so that the suture needle returns to the bent seagull shaped configuration shown in FIG. 5B so that the suture needle may be removed through the elongated conduit 132 of the trocar 130. In one embodiment, the needle driver may clamp onto the tip of the suture needle, the elongated body of the suture needle, the suture attachment barrel, or the suture attached to the proximal end of the suture needle for extracting and/or pulling the suture needle through the trocar to remove the suture needle from the surgical cavity.

Figure 6:
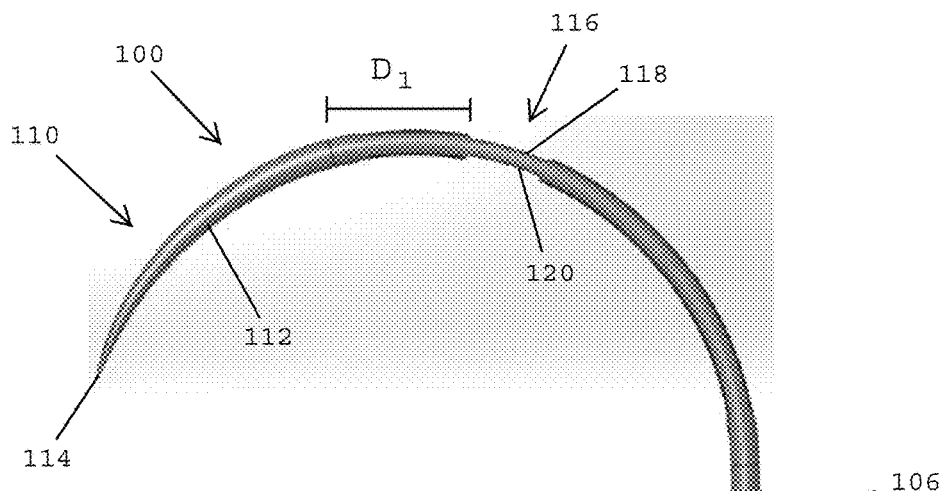
FIG. 6 shows a side view of a suture needle having a bendable region with a reduced diameter section that is midway between a distal point and a proximal end of the needle, in accordance with one embodiment of the present patent application.

In one embodiment, the location of the bendable region between the proximal and distal sections of the elongated body may be modified to provide the suture needle with different performance characteristics. Referring to FIG. 6, in one embodiment, the first and second flat surfaces 118, 120 that form the bendable region 116 are desirably located in the middle of the elongated body 102, about midway between the proximal end 106 of the elongated body and the distal tip 114. The bendable region 116 is spaced a distance $D_1$ from the beginning of the proximal end of the tapered region 112 of the elongated body 102.

Figure 7:
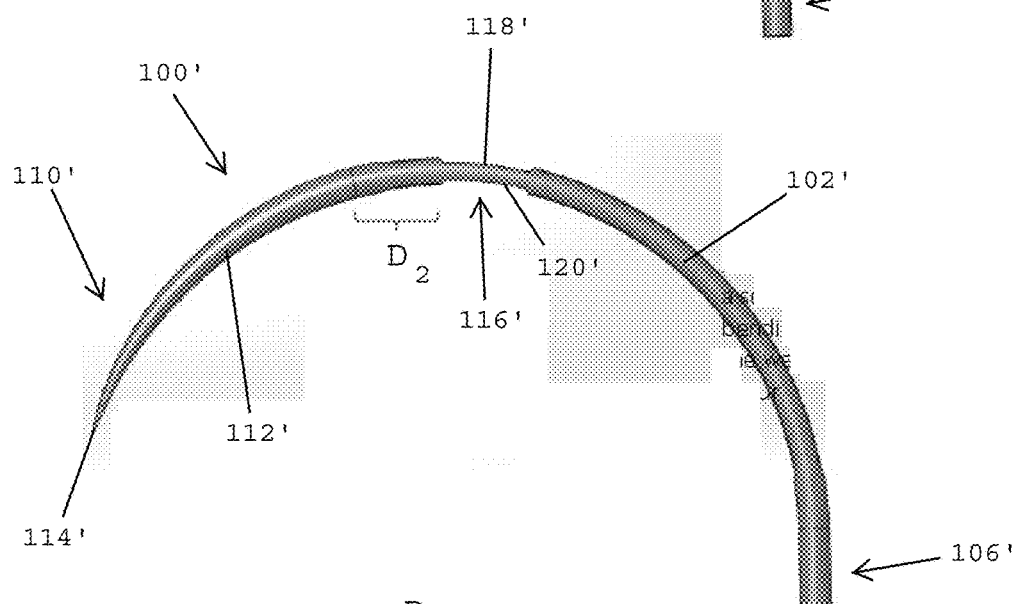
FIG. 7 shows a side view of a suture needle having a bendable region with a reduced diameter section that is midway between the tip and the suture barrel, in accordance with one embodiment of the present patent application.

Referring to FIG. 7, in one embodiment, a bendable suture needle 100' includes a bendable region 116' defined by first and second flat surfaces 118', 120', which are located closer to the sharpened tip 114' of the needle than the proximal end 106' of the needle. In the embodiment of FIG. 7, the bendable region 116' is spaced a distance $D_2$ from the beginning of the proximal end of the tapered region 112', which is smaller than the distance $D_1$ shown in FIG. 6.

Figure 8:
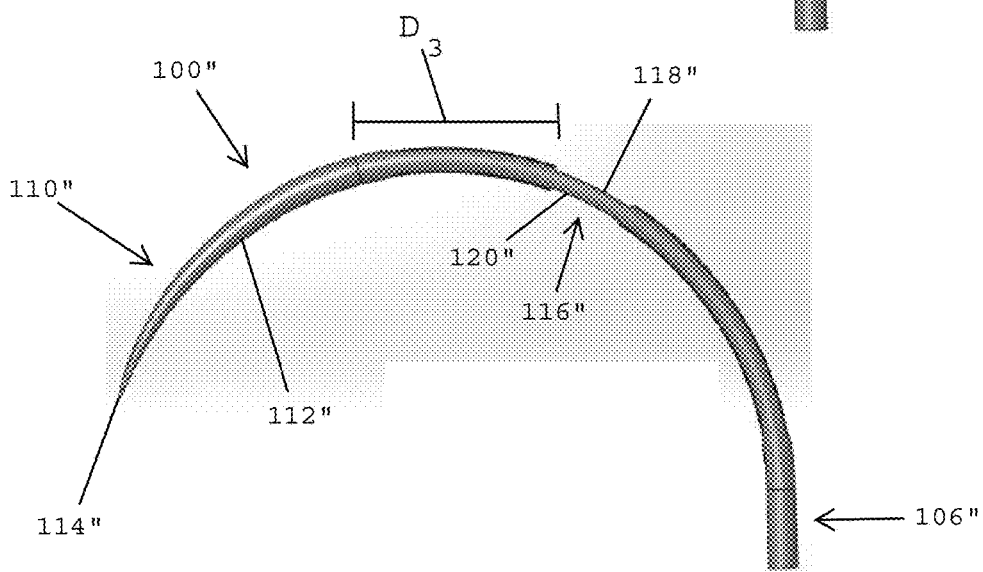
FIG. 8 shows a side view of a suture needle having a bendable region with a reduced diameter section that is closer to the proximal end of the needle, in accordance with one embodiment of the present patent application.

Referring to FIG. 8, in one embodiment, a suture needle 100" has the bendable region 116" located closer to the proximal end 106" of the needle than the sharpened tip 114" of the needle. In the embodiment of FIG. 8, the bendable region 116" is spaced a distance $D_3$ from the beginning of the proximal end of the tapered region 112", which is greater than the distance $D_2$ shown in FIG. 7.

Figure 9:
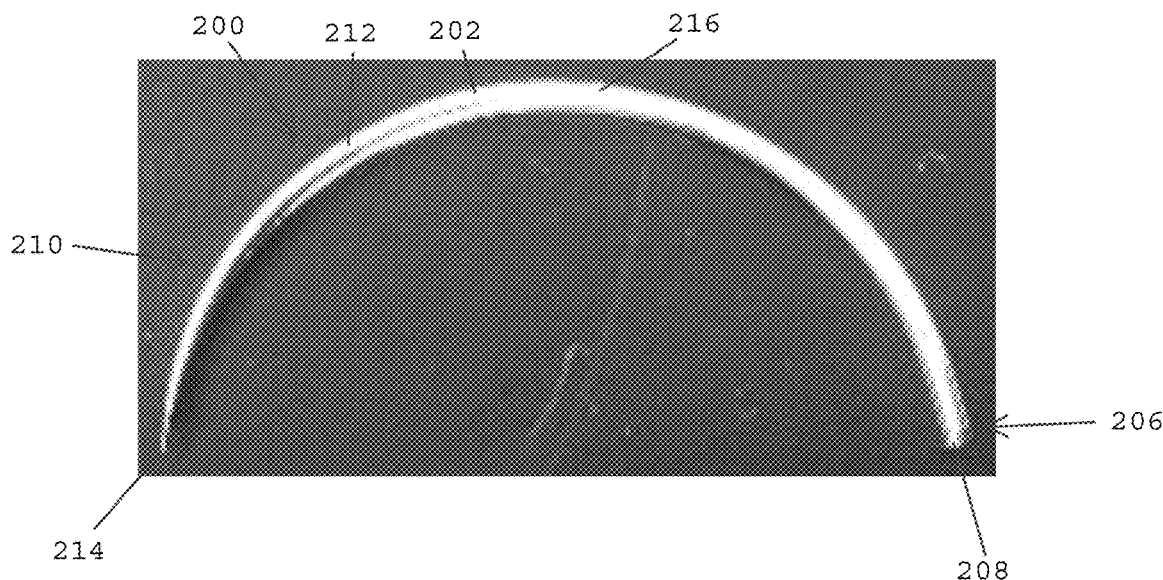
FIG. 9 shows a side view of a suture needle having a bendable region located between proximal and distal ends of the needle, in accordance with one embodiment of the present patent application.

Referring to FIG. 9, in one embodiment, a bendable suture needle 200 preferably includes an elongated body 202 having an outer surface 204. In one embodiment, the elongated body 202 extends from a proximal end 206 having a suture attachment barrel 208 that defines a proximal-most end of the suture needle and a distal end 210 having a tapered region 212 with a sharpened tip 214 that defines a distal-most end of the suture needle 200. In one embodiment, the suture needle 200 preferably includes a bendable region 216 that is located approximately midway along the length of the elongated body 202 of the needle between the proximal end 208 and the sharpened distal tip 214.

In one embodiment, the bendable region 216 may be formed by using heat such as heat treatment of martensitic, martensitic-aged, or austenitic steel alloys or the like. The softened, bendable region 116 may be located in the middle of the suture needle, or may be offset from the middle of the suture needle (e.g., somewhat closer to the distal point or the proximal barrel of the suture needle). Using a heat treatment to soften the metal or alloy and provide increased reshape ductility to the bendable region may be applied in conjunction with the mechanical processes described herein (e.g., providing flat surfaces to form a reduced diameter section shown in FIGS. 1-8). In one embodiment, temperatures in a range of 700-1100 Celsius may be used to achieve the softening and/or flexibility of the bendable region 216.

In one embodiment, a suture needle may have a composite structure including a softer, more flexible material and a more rigid material. In one embodiment, the proximal and distal sections of the elongated body of the needle may be made of a more rigid material such as stainless steel and the bendable section of the needle may be made of a more bendable material such as super elastic materials including Nitinol. Due to the composite nature of the needle, the outer surface of the needle will have the appearance of a normal, stainless steel needle, however, the bendable section is preferably made of a material (e.g., Nitinol) that is different than the material (e.g., stainless steel) used to make the ends of the needle.

Figure 10A:
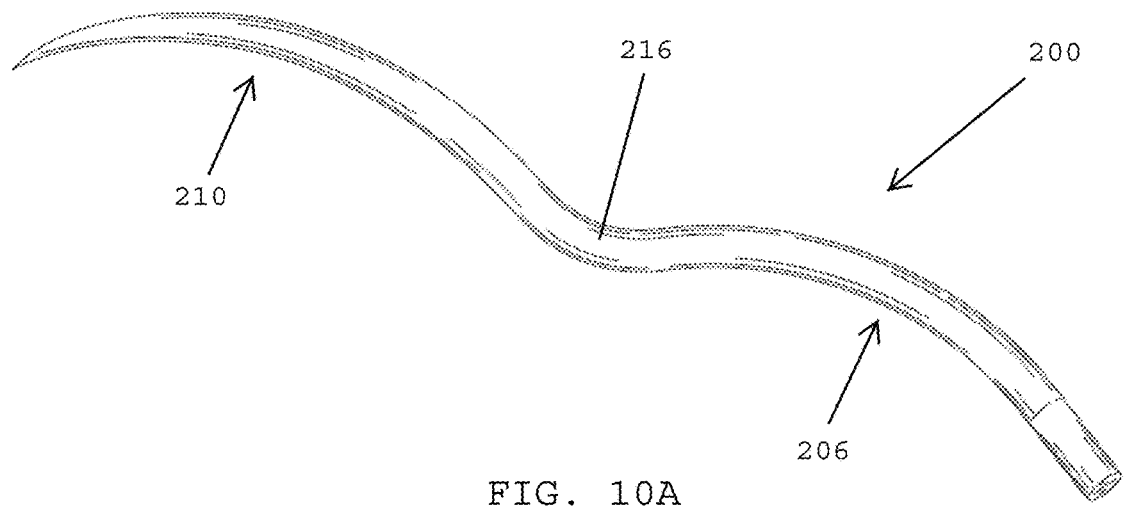
FIG. 10A shows a perspective view of the suture needle in FIG. 9 after it has been bent at the bendable region, in accordance with one embodiment of the present patent application.
Figure 10B:
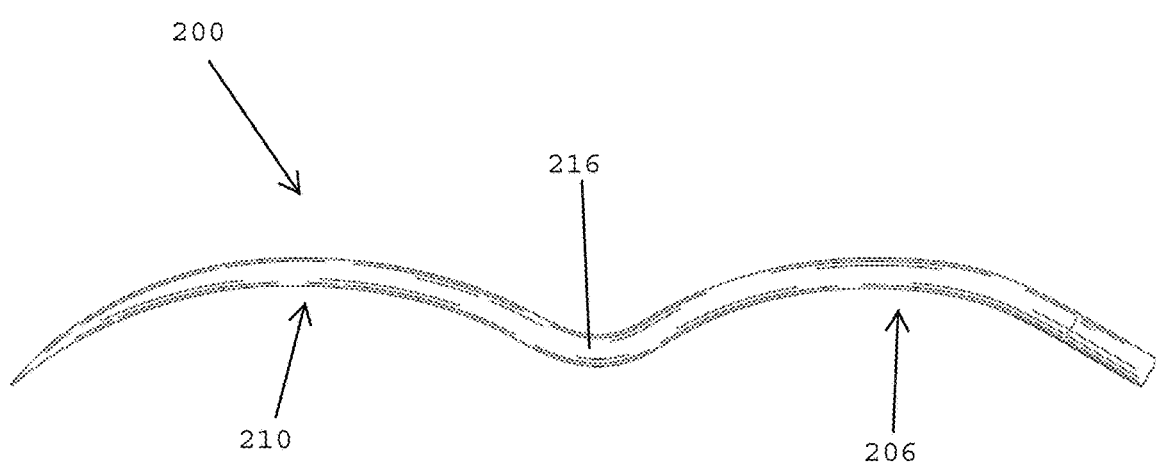
FIG. 10B shows a side view of the bent suture needle shown in FIG. 10A.

In one embodiment, the needle shown and described above in FIG. 9 may be transformed from a semi-circular or half-circle shaped configuration to a bent configuration having a seagull shape. Referring to FIG. 10A, in one embodiment, the suture needle 200 may be bent at the bendable region 216 to provide the needle with a seagull shaped configuration. In the seagull shaped configuration of FIGS. 10A and 10B, the suture needle 200 preferably has a smaller height or lower profile than the suture needle in the unbent configuration shown and described above in FIG. 9. The bendable region 216 is preferably more bendable and less rigid than the proximal and distal sections of the elongated body of the suture needle. As such, the proximal and distal sections of the suture needle preferably maintain their original shape in both the unbent configuration (FIG. 9) and the bent configuration (FIG. 10A).

In one embodiment, the suture needle 200 shown in FIG. 9 may also be folded in half at the bendable region 216 so that the distal tip 214 is positioned adjacent the barrel 208 at the proximal end 206 of the needle, which reduces the size of the needle so that it may be passed through a smaller trocar (e.g., a 5 mm trocar).

Figure 11A:
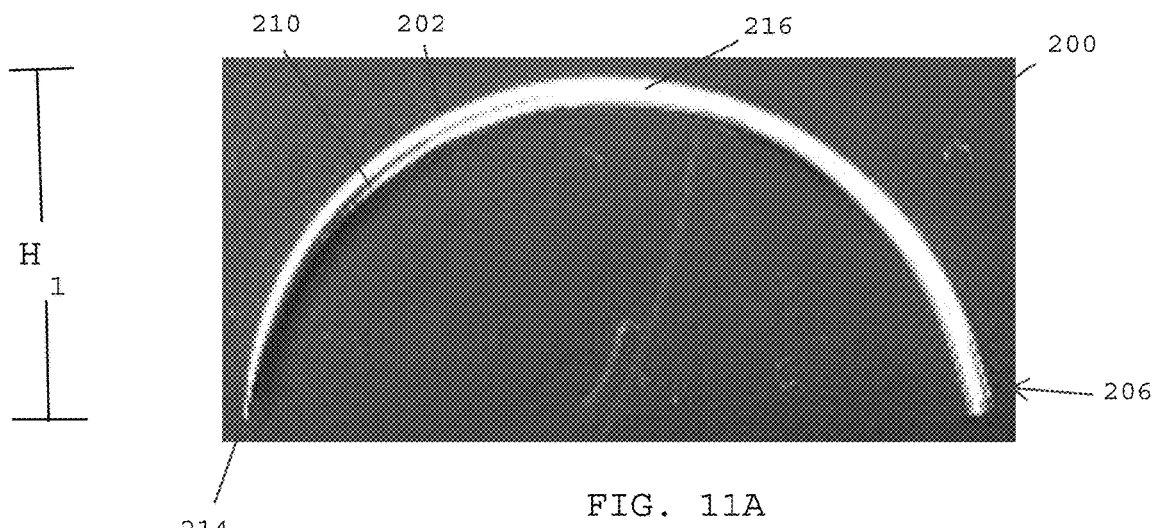
FIG. 11A shows a first stage of a method of passing a suture needle through a trocar, in accordance with one embodiment of the present patent application.

Referring to FIG. 11A, in one embodiment, the bendable suture needle 200 has a bendable region 216 that is preferably located between the proximal end 206 and the sharpened tip 214 at the distal end 210 thereof. In the unbent configuration of FIG. 11A, the elongated body 202 of the suture needle 200 defines a height $H_1$ of about Referring to FIG. 11B, in one embodiment, the suture needle 200 may be bent at the bendable region 216 to reshape the suture needle into a seagull shaped configuration. In the bent, seagull shaped configuration of FIG. 11B, the suture needle 200 has an elongated body 202 that defines a height $H_2$ that is less than the original height $H_1$ when the suture needle is in an unbent configuration. In one embodiment, in the bent, seagull shaped configuration shown in FIG. 11B, the suture needle 200 may be passed through a trocar for reaching a surgical site.

Figure 11B:
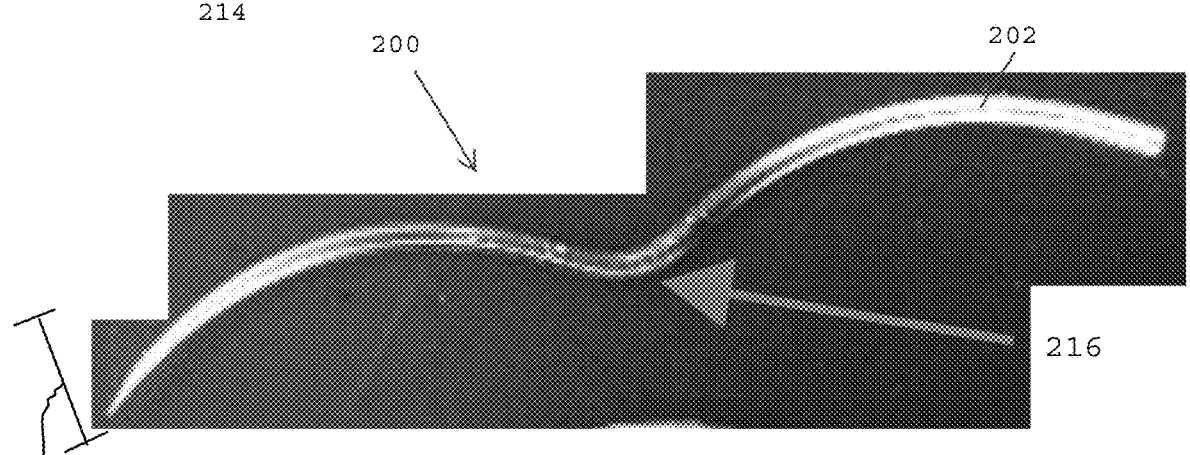
FIG. 11B shows a second stage of a method of passing a suture needle through a trocar, in accordance with one embodiment of the present patent application.
Figure 11C:
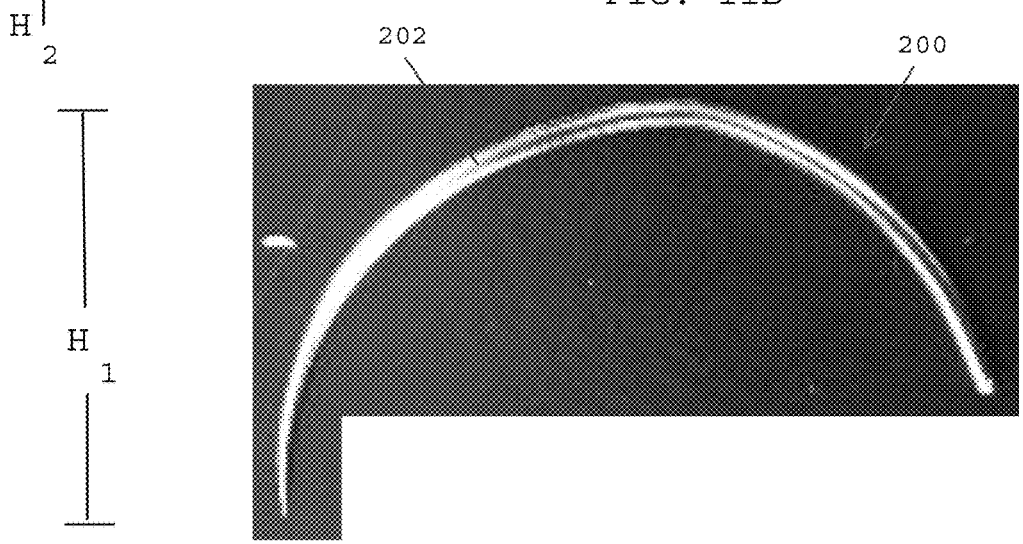
FIG. 11C shows a third stage of a method of passing a suture needle through a trocar, in accordance with one embodiment of the present patent application.

Referring to FIG. 11C, after the bent suture needle of FIG. 11B has been fully passed through a trocar and has reached the surgical site, a surgeon may use tools to engage the elongated body 202 of the suture needle to return the elongated body back to its original, unbent, semi-circular shape (FIG. 11A). In the original, unbent configuration shown in FIG. 11C, a surgeon may use the suture needle 200 for performing a suturing operation at a surgical site. After the suturing procedure has been completed, a surgeon may again bend the needle back to the seagull shaped configuration for removing the needle from the a patient's body via a trocar.

Figure 12:
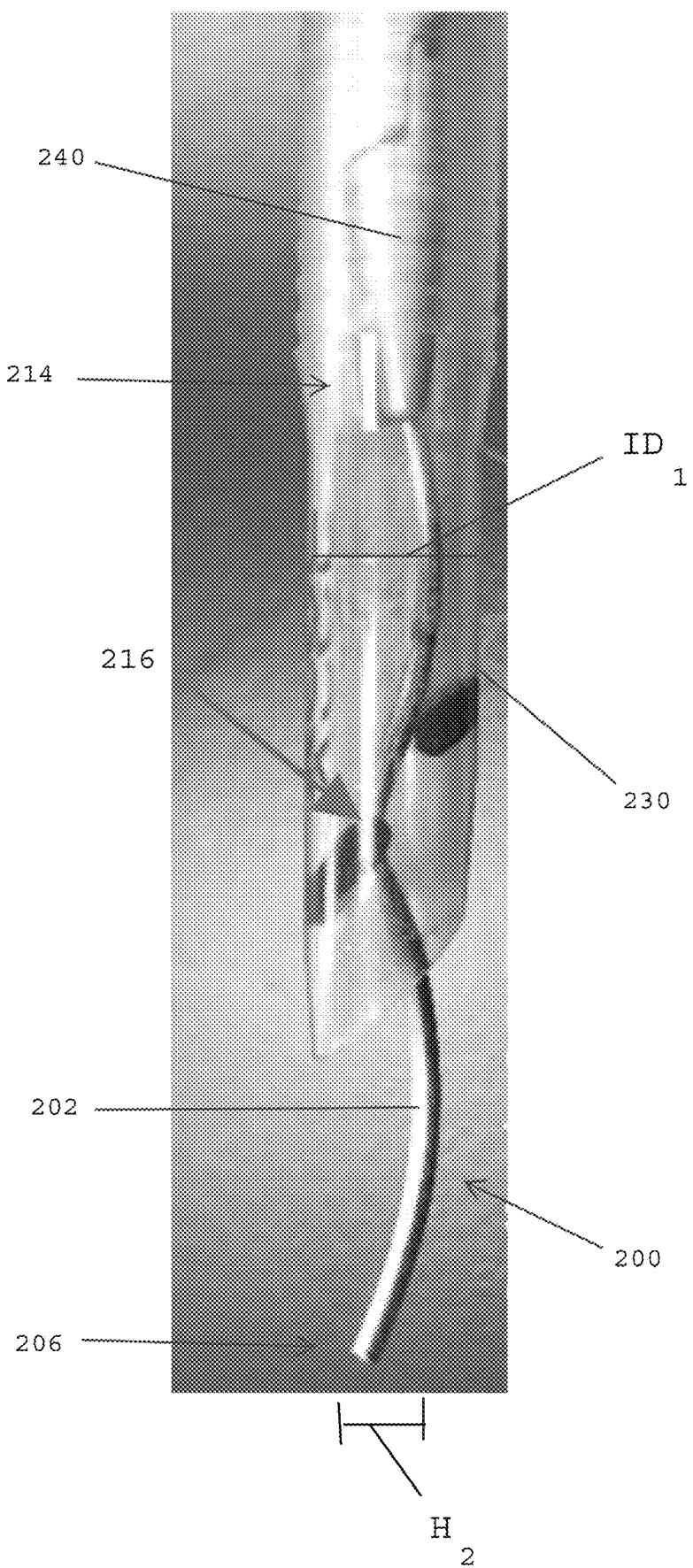
FIG. 12 shows the bent suture needle of FIG. 11B being passed through a trocar, in accordance with one embodiment of the present patent application.

Referring to FIG. 12, in one embodiment, with the bendable region 216 of the suture needle 200 being bent to place the suture needle 200 in the bent, seagull shaped configuration, the suture needle 200 may be passed through a trocar 230. In FIG. 12, the bent suture needle 200 having the seagull shaped configuration defines a height $H_2$ that is less than the inner diameter $ID_1$ of the cannula of the trocar 230 so that the bent suture needle 200 may be easily passed through the length of the trocar for reaching a surgical site, without damaging the needle or creating an unsafe condition for a patient.

In one embodiment, the sharpened tip 214 (FIG. 11A) of the suture needle 200 may be grasped by a surgical tool 240 (e.g., a needle driver) for passing the suture needle 200 through the trocar 230. In one embodiment, as the needle is passed through the trocar 230, the proximal end 206 of the elongated body 202 (e.g., the end of the needle with the suture hole) defines the leading end of the suture needle, and the sharpened tip 214 (FIG. 11A) at the proximal end 206 of the needle defines the trailing end of the needle so that the sharpened tip may be protected or covered as it passes through the elongated conduit of the trocar 230.

Referring to FIGS. 13A-13C, in one embodiment, a bendable suture needle 300 preferably includes an elongated body 302 having an outer surface 304. The elongated body 302 of the suture needle 300 preferably has a proximal end 306 having a suture attachment barrel 308 with a suture hole (not shown) and a distal end 310 including a tapered region 312 that terminates at a sharpened distal point 314 that defines a distal-most end of the bendable suture needle 300. In one embodiment, the suture needle 300 includes a bendable region 316 defined by first and second flat surfaces 318, 320 that are formed in the lateral sides of the elongated body 302. The flat surfaces 318, 320 preferably define a reduced cross-section region of the elongated body 302 that makes the bendable region 316 more flexible and/or bendable than the larger diameter proximal and distal sections 306, 310 of the suture needle 300. Referring to FIG. 13B, the proximal and distal sections 306, 310 of the elongated body 302 define respective outer diameters $OD_3$ that are greater than the diameter $OD_4$ of the bendable region 316 of the elongated body 302.

In one embodiment, the length of the first and second flat surfaces 318, 320 that form the bendable region 316 of the needle 300 desirably define a length $L_2$ that is equal to or greater than the outer diameter $OD_3$ of the respective proximal and distal sections 306, 310 of the elongated body 302.

Figure 14A:
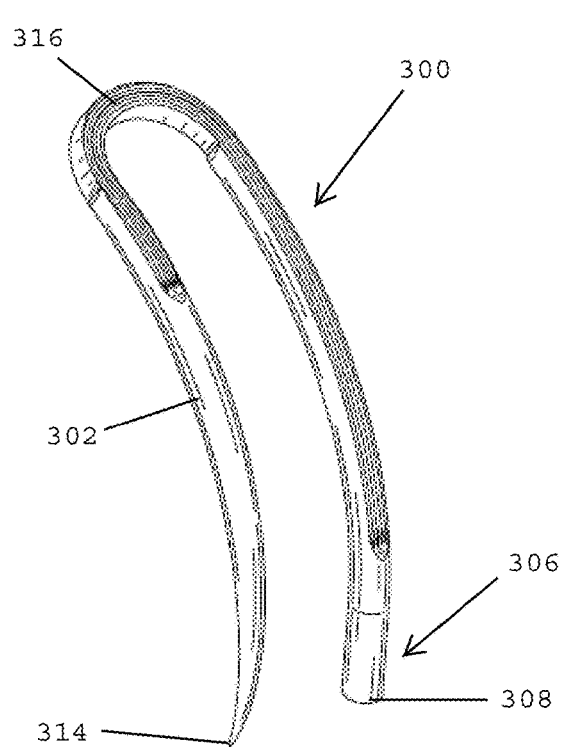
FIG. 14A shows a perspective view of the suture needle of FIGS. 13A-130 in a bent configuration, in accordance with one embodiment of the present patent application.
Figure 14B:
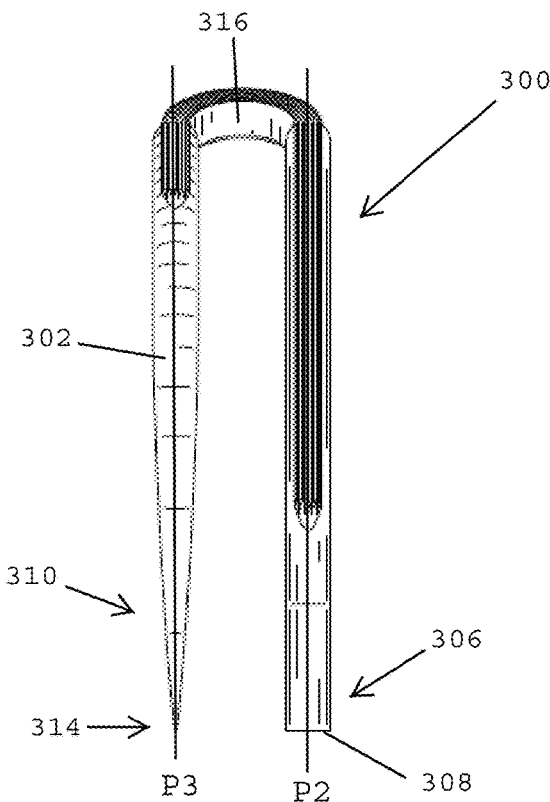
FIG. 14B shows an end view of the bent suture needle shown in FIG. 14A.
Figure 14C:
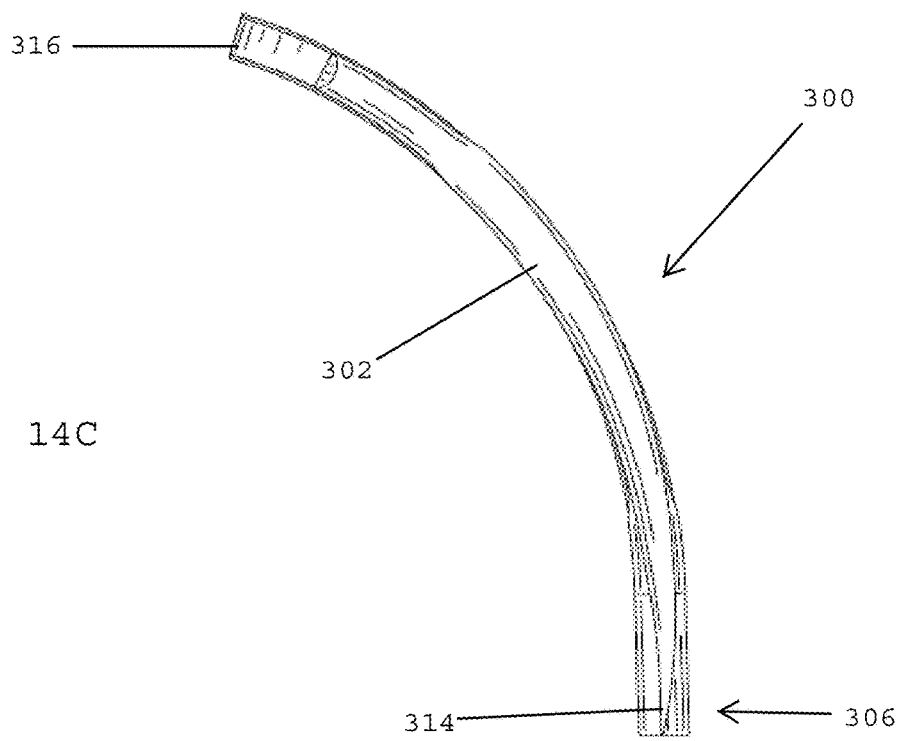
FIG. 14C shows a side view of the bent suture needle shown in FIGS. 14A and 14B.

Referring to FIGS. 14A-14C, in one embodiment, the suture needle 300 of FIGS. 13A-13C may be bent or folded at the bendable region 316 so that the sharpened tip 314 of the suture needle is adjacent the suture attachment barrel 308 located at the proximal end 306 of the elongated body 302. In the bent or folded configuration shown in FIGS. 14A-14C, the elongated body 302 of the suture needle 308 has a smaller height, dimension and/or profile than when the suture needle is an unbent, semi-circular configuration.

Referring to FIG. 14B, in one embodiment, when the elongated body 302 has been bent into the folded configuration, the elongated body 302 is folded in half so that the proximal section 306 of the elongated body 302 preferably lies in a first plane P2 and the distal section 310 of the elongated body preferably lies in a second plane P3 that is different than the first plane P2. In one embodiment, the planes P2 and P3 are preferably parallel to one another. In the folded configuration, the bendable region 316 desirably interconnects inner ends of the respective proximal and distal sections 306, 310 of the elongated body 302.

Referring to FIG. 15A, in one embodiment, a bendable suture needle 300 having a bendable region 316 is in an unbent, semi-circular configuration (i.e., FIGS. 13A-13C). In the unbent configuration, the elongated body 302 of the suture needle 300 defines a height $H_3$ of about greater than 5 mm, more preferably about 10-15 mm, and even more preferably about 13 mm.

Referring to FIG. 15B, in one embodiment, the bendable suture needle 300 may be transformed from the larger, unbent configuration shown in FIGS. 13A-13C to the smaller, bent configuration shown in FIGS. 14A-14C so that the elongated body 302 of the suture needle 300 defines a height $H_4$ of about 5 mm or less, which is significantly smaller than the height $H_3$ when the suture needle is in the unbent configuration (FIG. 15A). As a result, the suture needle 300 may pass through an opening of a smaller trocar (e.g., 5 mm trocar) when the suture needle is the bent configuration. The same suture needle cannot pass through the smaller trocar when the suture needle is in the unbent configuration.

Referring to FIGS. 16A-16C, in one embodiment, a bendable suture needle 400 preferably has an elongated body 402 with a proximal end 406 and a distal end 410 having a sharpened tip 414. The bendable suture needle 400 preferably includes a bendable region 416 that may be achieved via heat treatment of martensitic, martensitic-aged, or austenitic steel alloys or the like. The bendable region 416 may be in the middle or offset from the middle of the elongated body 402 of the needle. In one embodiment, a suture needle may be a composite of a superelastic material and stainless steel. In one embodiment, the bendable region 416 of the suture needle 400 may be made of super elastic materials having shape memory properties (e.g., Nitinol), while the proximal and distal ends 406, 410 of the elongated body 402 comprise more rigid, inflexible materials such as stainless steel.

In the bent configuration shown in FIG. 16A-16C, the suture needle may be passed through a trocar to a surgical site. Once the suture needle 400 has reached the surgical site, a surgeon may use surgical tools to transform the bent suture needle to an unbent, semi-circular configuration as shown and described herein (e.g., the embodiment of FIG. 15A). Once a suturing operation has been completed at the surgical site, a surgeon may once again bend the suture needle 400 at the bendable region 416 for reducing the dimension of the needle to remove the suture needle from the surgical site via a trocar.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A suture needle having a bendable region comprising:
   an elongated body having a proximal section with a suture attachment hole and a distal section with a sharpened tip;
   said elongated body having a bendable region located between said proximal and distal sections, wherein said bendable region of said elongated body is more flexible than said proximal and distal sections of said elongated body for enabling said elongated body of said suture needle to be transformed from a first configuration having a greater dimension and a second configuration having a smaller dimension;

wherein said elongated body has a greater height and a semi-circular shape when in the first configuration and a smaller height and a folded shape when in the second configuration;

wherein said elongated body in the second configuration having the folded shape comprises said proximal section of said elongated body lying in a first plane, said distal section of said elongated body lying in a second plane that is different than the first plane, and said bendable region of said elongated body interconnecting inner ends of said proximal and distal sections of said elongated body, wherein with said elongated body in the second configuration having the folded shape said sharpened tip of said distal section of said elongated body is adjacent said suture attachment hole of said proximal section of said elongated body.

2. The suture needle as claimed in claim 1, wherein said proximal and distal sections of said elongated body define a first outer diameter and said bendable region of said elongated body defines a second outer diameter that is smaller than the first outer diameter of said respective proximal and distal sections.

3. The suture needle as claimed in claim 2, wherein said bendable region of said elongated body comprises one or more flat surfaces located on opposite sides of said elongated body that define a reduced cross-sectional region of said elongated body having a dimension that is smaller than the first outer diameter of said respective proximal and distal sections of said elongated body.

4. The suture needle as claimed in claim 3, wherein said one or more flat surfaces comprise first and second flat surfaces located on respective first and second lateral sides of said elongated body.

5. The suture needle as claimed in claim 1, wherein said bendable region of said elongated body comprises a superelastic material and said proximal and distal sections of said elongated body comprise a second material that is more rigid and less elastic than said superelastic material.

6. The suture needle as claimed in claim 5, wherein said superelastic material comprises Nitinol and said second material comprises stainless steel.

7. The suture needle as claimed in claim 2, wherein said bendable region of said elongated body comprises a superelastic material and said proximal and distal sections of said elongated body comprise a second material that is more rigid and less elastic than said superelastic material of said bendable region.

8. The suture needle as claimed in claim 7, wherein said superelastic material comprises Nitinol and said second material comprises stainless steel.

9. A suture needle having a bendable region comprising:
an elongated body having a proximal section with a suture attachment hole and a distal section with a sharpened tip;
said elongated body having a bendable region located between said proximal and distal sections, wherein said bendable region of said elongated body comprises a superelastic material and said proximal and distal sections of said elongated body comprise a second material that is more rigid and less elastic than said superelastic material for enabling said suture needle to be transformed from a first configuration having a greater dimension and a second configuration having a smaller dimension.

10. The suture needle as claimed in claim 9, wherein said proximal and distal sections of said elongated body define a first outer diameter and said bendable region of said elongated body defines a second outer diameter that is smaller than the first outer diameter of said respective proximal and distal sections.

11. The suture needle as claimed in claim 10, wherein said bendable region of said elongated body comprises one or more flat surfaces located on opposite sides of said elongated body that define a reduced cross-sectional region of said elongated body having a dimension that is smaller than the first outer diameter of said respective proximal and distal sections of said elongated body.

12. The suture needle as claimed in claim 9, wherein said elongated body has a semi-circular shape and a greater height when in the first configuration and a folded shape with the smaller height when in the second configuration.

13. The suture needle as claimed in claim 9, wherein said elongated body in the second configuration has a folded shape comprising:
said proximal section of said elongated body lying in a first plane;
said distal section of said elongated body lying in a second plane that is different than the first plane;
said bendable region of said elongated body interconnecting inner ends of said proximal and distal sections of said elongated body, wherein with said elongated body in the second configuration having the folded shape said sharpened tip of said distal section of said elongated body is adjacent said suture attachment hole of said proximal section of said elongated body.

14. The suture needle as claimed in claim 13, wherein said proximal and distal sections of said elongated body define a first outer diameter and said bendable region of said elongated body defines a second outer diameter that is smaller than the first outer diameter of said respective proximal and distal sections of said elongated body.

15. A suture needle having a bendable region comprising:
an elongated body having a proximal section with a suture attachment hole and a distal section with a sharpened tip;
said elongated body having a bendable region located between said proximal and distal sections, wherein said bendable region of said elongated body is more flexible than said proximal and distal sections of said elongated body for enabling said elongated body of said suture needle to be transformed between an unfolded configuration having a semi-circular shape with a greater height and a folded configuration having a folded shape with a smaller height, wherein in the folded configuration said proximal section of said elongated body lies in a first plane and said distal section of said elongated body lies in a second plane that is different than the first plane so that said sharpened tip of said distal section of said elongated body is adjacent said suture attachment hole of said proximal section of said elongated body.

16. The suture needle as claimed in claim 15, wherein said proximal and distal sections of said elongated body define a first outer diameter and said bendable region of said elongated body defines a second outer diameter that is smaller than the first outer diameter of said respective proximal and distal sections.

17. The suture needle as claimed in claim 15, wherein said bendable region of said elongated body comprises one or more flat surfaces located on opposite sides of said elongated body that define a reduced cross-sectional region of said elongated body having a dimension that is smaller than the first outer diameter of said respective proximal and distal sections of said elongated body.

18. The suture needle as claimed in claim 17, wherein said one or more flat surfaces comprise first and second flat surfaces located on respective first and second lateral sides of said elongated body.

19. The suture needle as claimed in claim 15, wherein said bendable region of said elongated body comprises a superelastic material and said proximal and distal sections of said elongated body comprise a second material that is more rigid and less elastic than said superelastic material.

20. The suture needle as claimed in claim 19, wherein said superelastic material comprises Nitinol and said second material comprises stainless steel.

\* \* \* \* \*